US012731258B2

(12) United States Patent
Castillo et al.

(10) Patent No.: US 12,731,258 B2
(45) Date of Patent: Sep. 8, 2026

(54) SYSTEMS AND METHODS FOR IMAGE PROCESSING TO IDENTIFY PATIENTS WITH PULMONARY EMBOLISM

(71) Applicant: William Beaumont Hospital, Royal Oak, MI (US)

(72) Inventors: Edward Castillo, Austin, TX (US); Girish B. Nair, West Bloomfield, MI (US)

(73) Assignee: William Beaumont Hospital, Royal Oak, MI (US)

( * ) Notice: Subject to any disclaimer, the term of this patent is extended or adjusted under 35 U.S.C. 154(b) by 173 days.

(21) Appl. No.: 18/683,852

(22) PCT Filed: Sep. 2, 2022

(86) PCT No.: PCT/US2022/042456
§ 371 (c)(1),
(2) Date: Feb. 15, 2024

(87) PCT Pub. No.: WO2023/034570
PCT Pub. Date: Mar. 9, 2023

(65) Prior Publication Data

US 2024/0296566 A1 Sep. 5, 2024

Related U.S. Application Data

(60) Provisional application No. 63/240,453, filed on Sep. 3, 2021.

(51) Int. Cl.

| | |
|---|---|
| ***G06K 9/00*** | (2022.01) |
| ***A61B 6/03*** | (2006.01) |

(Continued)

(52) U.S. Cl.
CPC ............ *G06T 7/0014* (2013.01); *A61B 6/032* (2013.01); *A61B 6/507* (2013.01); *G06T 7/11* (2017.01);
(Continued)

(58) Field of Classification Search
CPC ..................... G06T 7/0014; G06T 7/11; G06T 2207/10076; G06T 2207/20021;
(Continued)

(56) References Cited

U.S. PATENT DOCUMENTS 6,813,333 B2 11/2004 Karau
8,538,111 B2 * 9/2013 Zhang .................... A61B 5/091 382/131

(Continued)

FOREIGN PATENT DOCUMENTS

JP 2011-212313 A 10/2011
JP 2019-528116 A 10/2019

(Continued)

OTHER PUBLICATIONS

Fujita, Yukio, et al. "Combined Assessment of Pulmonary Ventilation and Perfusion with Single-Energy Computed Tomography and Image Processing", Academic Radiology, Elsevier Inc. US, vol. 28, No. 5, Jun. 10, 2020, pp. 636-646.

(Continued)

*Primary Examiner* — Gregory A Morse
*Assistant Examiner* — Owais I Memon
(74) *Attorney, Agent, or Firm* — Honigman LLP; Thomas J. Appledorn

(57) ABSTRACT

A method for processing images of lungs including defining lung segmentation of the lungs, performing deformable image registration on the segmented lungs, performing ventilation estimation operations to determine a ventilation estimation, performing perfusion estimation operations to (Continued)

determine a perfusion estimation, comparing the ventilation estimation to the perfusion estimation, and determining a pulmonary embolism risk score based on the comparison of the ventilation estimation to the perfusion estimation.

20 Claims, 3 Drawing Sheets

(51) Int. Cl.

*A61B 6/50* (2024.01)
*G06T 7/00* (2017.01)
*G06T 7/11* (2017.01)
*G16H 50/30* (2018.01)

(52) U.S. Cl.

CPC ... *G16H 50/30* (2018.01); *G06T 2207/10076* (2013.01); *G06T 2207/20021* (2013.01); *G06T 2207/30061* (2013.01)

(58) Field of Classification Search

CPC . G06T 2207/30061; G06T 2207/10081; G06T 2207/20084; G06T 7/0016; A61B 6/032; A61B 6/507; A61B 5/026; A61B 5/055; A61B 5/7264; A61B 2576/02; A61B 5/7275; A61B 5/08; G16H 50/30; G16H 30/40; G16H 50/20

See application file for complete search history.

(56) References Cited

U.S. PATENT DOCUMENTS

2002/0198449 A1 12/2002 Baumgardner et al.
2013/0338489 A1 12/2013 Prisk et al.
2019/0183444 A1* 6/2019 Castillo .................... G06T 7/37
2021/0015078 A1 1/2021 Bray
2022/0254016 A1* 8/2022 Hoffman ............. A61B 6/5217

FOREIGN PATENT DOCUMENTS

WO WO-2018157191 A1 * 9/2018 ............. G16H 50/20
WO 2020231904 A1 11/2020

OTHER PUBLICATIONS

Nair, Girish B., et al. "A prospective study to validate pulmonary blood mass changes on non-contrast 4DCT in pulmonary embolism patients", Clinical Imaging, Elsevier, New York, NY US, vol. 78, Mar. 5, 2021, pp. 179-183.

"SAEM Annual Meeting Abstracts", Academic Emergency Medicine, Hanley and Belfus, Philadelphia, PA, US, vol. 26, Apr. 22, 2019, pp. S9-S304.

Supplementary European Search Report for EP22865606 dated May 13, 2025.

Dec. 23, 2022 PCT ISR & Written Opinion for PCT/US2022/042456, 8 pages.

Turner-Lawrence, Danielle, et al. "Detecting Pulmonary Embolism from Non-Contrast Computed Tomography", SAEM Annual Meeting Abstracts 2019 Academic Emergency Medicine, SAEM, Apr. 22, 2019, p. S276-S277.

* cited by examiner

SYSTEMS AND METHODS FOR IMAGE PROCESSING TO IDENTIFY PATIENTS WITH PULMONARY EMBOLISM

CROSS REFERENCE TO RELATED APPLICATIONS

This patent application is a 35 U.S.C. § 371 United States National Phase Stage of, and claims the benefit of PCT International Application No. PCT/US2022/042456 filed Sep. 2, 2022, which claims the benefit under 35 U.S.C. § 119(e) to U.S. Provisional Application 63/240,453, filed Sep. 3, 2021. The disclosures of the prior applications are considered part of the disclosures of these applications and are hereby incorporated by reference in their entireties.

TECHNICAL FIELD

This disclosure relates to systems and methods for image processing-based pulmonary embolism detection.

BACKGROUND

Pulmonary Embolism (PE) is a major health problem in the United States. Mortality for acute PE is between 10-30% if left untreated, but can be reduced to 2-8% with prompt treatment. Accordingly, timely and accurate PE diagnosis is crucial to help save patient lives.

Computed Tomography Angiography (CTA), alone, or in combination with CT venous-phase imaging are currently used to indicate a positive indication of PE for patients with a high clinical probability (as indicated by either Wells or Geneva scores) or a negative indication of PE for patients with a low clinical probability. However, due to contraindications such as iodinated contrast allergy or renal insufficiency, 10-30% of patients are ineligible for CTA.

Nuclear medicine imaging is another method currently used to diagnose PE, but requires transporting the patient to the nuclear medicine clinic, which may not be available on nights and weekends. Nuclear medicine imaging requires a long scan acquisition time (i.e., one to two hours) and the scans may be difficult to reproduce. Accordingly, nuclear medicine imaging may not satisfy the time-sensitive requirements for diagnosing PE.

SUMMARY

One aspect of the disclosure provides a method for processing images of lungs comprising defining, via data processing hardware, lung segmentation of the lungs, performing, via the data processing hardware, deformable image registration on the segmented lungs, performing, via the data processing hardware, ventilation estimation operations to determine a ventilation estimation, performing, via the data processing hardware, perfusion estimation operations to determine a perfusion estimation, comparing, via the data processing hardware, the ventilation estimation to the perfusion estimation, and determining, via the data processing hardware, a pulmonary embolism risk score based on the comparison of the ventilation estimation to the perfusion estimation.

Implementations of the disclosure include one or more of the following aspects. In some implementations, the images of the lungs are obtained using non-contrast 4-dimensional computed tomography.

The method may further comprise receiving, via the data processing hardware, the images of the lungs.

The lungs may be segmented into five regions. The pulmonary embolism risk score may be on a scale from 0 to 5 based on the number of lung regions that have ventilation/perfusion mismatch. Ventilation/perfusion mismatch may be defined by:

$$B(\Omega_i; p_i, v_i) = \begin{cases} 0, \ Perf\,(\Omega_i) < p_i \text{ and Vent}\,(\Omega_i) < v_i \text{ (Matched Function)} \\ 0, \ Perf\,(\Omega_i) \geq p_i \text{ and Vent}\,(\Omega_i) \geq v_i \text{ (Matched Function)} \\ 1, \ Perf\,(\Omega_i) < p_i \text{ and Vent}\,(\Omega_i) \geq v_i \text{ (Mismatched Function)} \\ 1, \ Perf\,(\Omega_i) \geq p_i \text{ and Vent}\,(\Omega_i) < v_i \text{ (Mismatched Function)} \end{cases}.$$

Optimal threshold values may be determined by:

$$\max_{p,v} \frac{1}{|I_{pos}|} \sum_{j \in I_{pos}} F(s_j(p, v)) + \frac{1}{|I_{neg}|} \sum_{j \in I_{neg}} G(s_j(p, v)).$$

The optimal solution obtained from the above equation may be:

$$v^* = [\,0.12 \quad 0.15 \quad 0.15 \quad 0.11 \quad 0.12\,],$$

$$p^* = [\,0.03 \quad 0.10 \quad 0.07 \quad 0.01 \quad 0.13\,].$$

The pulmonary embolism risk score may be determined using one or more of artificial intelligence, machine learning, and a neural network.

The pulmonary embolism risk score may be determined by:

$$s(p, v) = \sum_{i=1}^{5} B(\Omega_i; p_i, v_i).$$

Another aspect of the disclosure provides a system comprising data processing hardware and memory hardware in communication with the data processing hardware, the memory hardware storing instructions that when executed on the data processing hardware cause the data processing hardware to perform operations comprising defining lung segmentation of the lungs, performing deformable image registration on the segmented lungs, performing ventilation estimation operations to determine a ventilation estimation, performing perfusion estimation operations to determine a perfusion estimation, comparing the ventilation estimation to the perfusion estimation, and determining a pulmonary embolism risk score based on the comparison of the ventilation estimation to the perfusion estimation.

Implementations of the disclosure include one or more of the following aspects. In some implementations, the images of the lungs are obtained using non-contrast 4-dimensional computed tomography.

The operations may include receiving the images of the lungs.

The lungs may be segmented into five regions. The pulmonary embolism risk score may be on a scale from 0 to 5 based on the number of lung regions that have ventilation/perfusion mismatch. Ventilation/perfusion mismatch may be defined by:

$$B(\Omega_i; p_i, v_i) = \begin{cases} 0, & Perf(\Omega_i) < p_i \text{ and } \mathrm{Vent}(\Omega_i) < v_i \text{ (Matched Function)} \\ 0, & Perf(\Omega_i) \geq p_i \text{ and } \mathrm{Vent}(\Omega_i) \geq v_i \text{ (Matched Function)} \\ 1, & Perf(\Omega_i) < p_i \text{ and } \mathrm{Vent}(\Omega_i) \geq v_i \text{ (Mismatched Function)} \\ 1, & Perf(\Omega_i) \geq p_i \text{ and } \mathrm{Vent}(\Omega_i) < v_i \text{ (Mismatched Function)} \end{cases}.$$

Optimal threshold values may be determined by:

$$\max_{p,v} \frac{1}{|I_{pos}|} \sum_{j \in I_{pos}} F(s_j(p, v)) + \frac{1}{|I_{neg}|} \sum_{j \in I_{neg}} G(s_j(p, v)).$$

The optimal solution obtained from the above equation may be:

$$v^* = [\,0.12 \quad 0.15 \quad 0.15 \quad 0.11 \quad 0.12\,],$$

$$p^* = [\,0.03 \quad 0.10 \quad 0.07 \quad 0.01 \quad 0.13\,].$$

The pulmonary embolism risk score may be determined using one or more of artificial intelligence, machine learning, and a neural network.

The pulmonary embolism risk score may be determined by:

$$s(p, v) = \sum_{i=1}^{5} B(\Omega_i; p_i, v_i).$$

DESCRIPTION OF DRAWINGS

Like reference symbols in the various drawings indicate like elements.

DETAILED DESCRIPTION

Example configurations will now be described more fully with reference to the accompanying drawings. Example configurations are provided so that this disclosure will be thorough, and will fully convey the scope of the disclosure to those of ordinary skill in the art. Specific details are set forth such as examples of specific components, devices, and methods, to provide a thorough understanding of configurations of the present disclosure. It will be apparent to those of ordinary skill in the art that specific details need not be employed, that example configurations may be embodied in many different forms, and that the specific details and the example configurations should not be construed to limit the scope of the disclosure.

Figure 1:
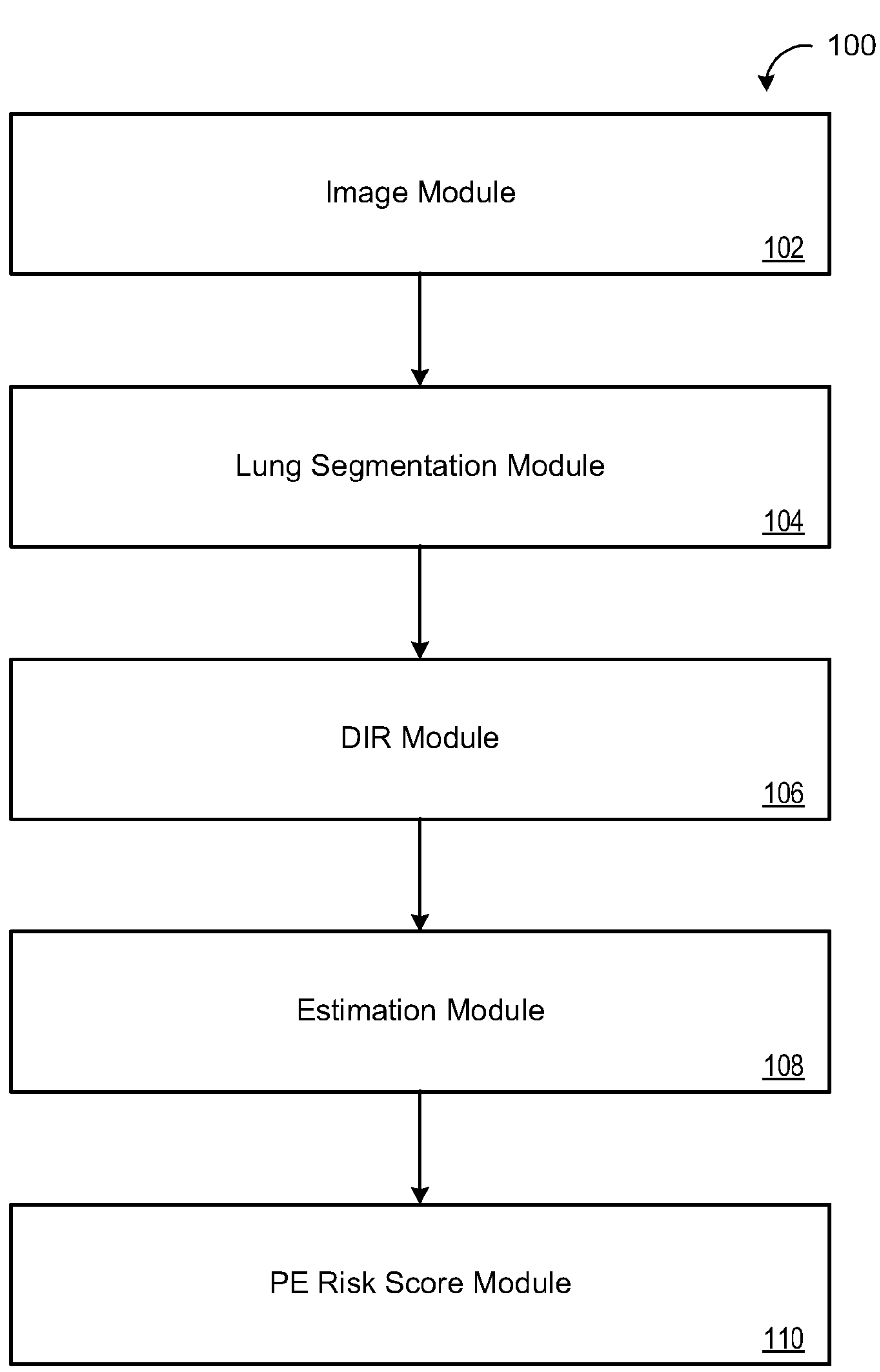
FIG. 1 is schematic of a system for processing images of lungs.
Figure 2:
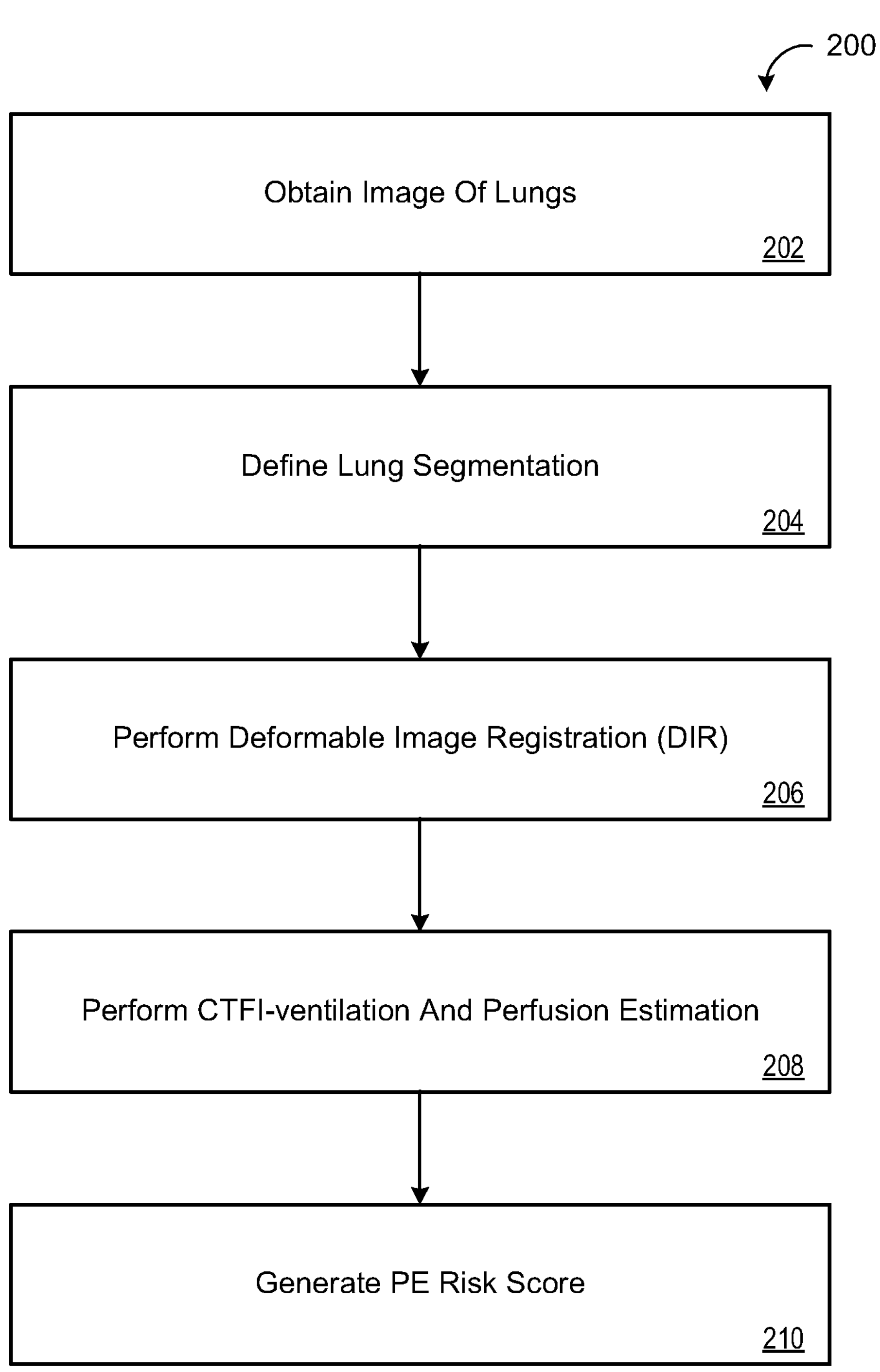
FIG. 2 is flowchart illustrating a method for processing images of lungs.
Figure 3:
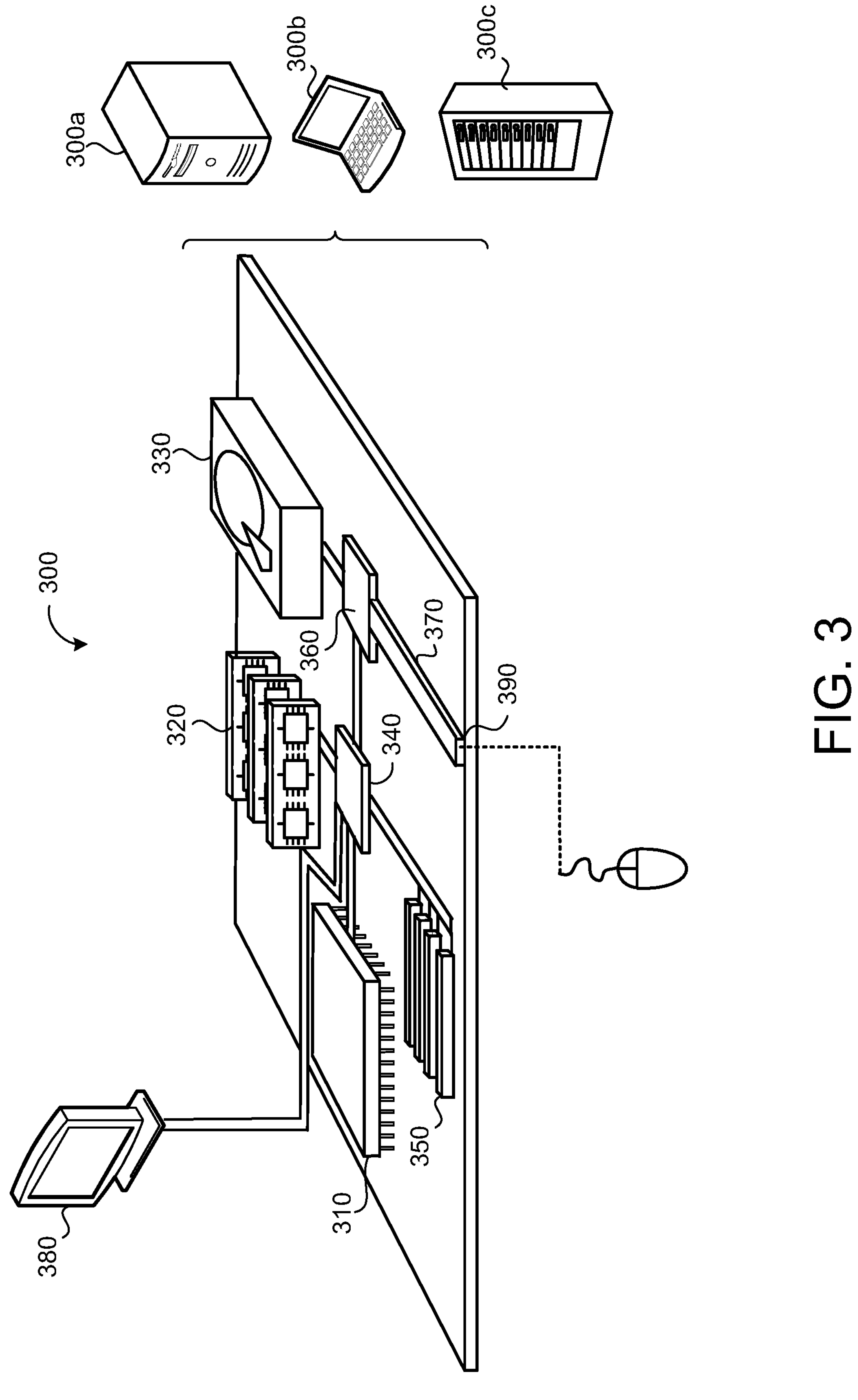
FIG. 3 is a schematic view of an example computing device that may be used to implement the systems and methods described herein.

Referring to FIGS. 1-3, systems and methods for processing images of lungs are generally shown. The systems and methods may include certain elements associated with magnetic resonance imaging (MRI) or Computed Tomography (CT)-derived ventilation imaging and image processing methods to produce non-contrast based MRI-ventilation (MR-vent) images and CT ventilation (CT-vent) images, respectively. In some implementations, the systems and methods described herein may receive or obtain the images from a third-party individual or entity or from any suitable source. In other implementations, the systems and methods may produce the images from lungs in a breathhold inhale position and an exhale position, from temporally resolved four-dimensional (4D) MRI sequences or 4DCT sequences, e.g., three-dimensional (3D) images across the fourth dimension, time, and/or using any of the systems and methods described in U.S. patent application Ser. No. 16/705,844, filed on Dec. 6, 2019, the disclosure of which is hereby incorporated by reference in its entirety.

Referring to FIG. 1, an exemplary system 100 for diagnosing PE using image processing is generally shown. The modules shown in FIG. 1 are provided for illustrative purposes only, and it should be understood that additional, fewer, or different modules may be provided as suitable. Additionally, it should be understood that the description of each module does not limit that description to a discrete module, and certain functions or operations may be performed by a combination of modules or in any suitable manner.

The system 100 includes an image module 102 configured to obtain or receive images of lungs obtained using CT-derived function imaging (CTFI), such as 4DCT. As set forth above, the image 100 may be obtained or produced in any suitable manner, including using any of the systems and methods described in U.S. patent application Ser. No. 16/705,844. In some implementations, the systems and methods described herein include generating CTFI images from reconstructed 4DCT inhale/exhale images for the patient.

The system 100 includes a lung segmentation module 104. In some implementations, the lung segmentation module 104 creates lung segmentation masks automatically using a DenseNet convolutional neural network trained on publicly available data or any other suitable data. The lung segmentation module 104 may divide or segment the lungs into five regions corresponding to the five lobes of the lungs. Specifically, the lung segmentation module 104 may segment the right lung into a superior lobe, a middle lobe, and an inferior lobe and the left lung into a superior lobe and an inferior lobe. In some implementations, the lung segmentation module 104 may determine an approximation of the five lobes, i.e., the lung segmentation module 104 may determine a total volume of each lung and may divide the right lung into equal thirds based on the total volume of the right lung, and the lung segmentation module 104 may approximate the superior lobe of the left lung to be two-thirds of the total volume of the left lung and the inferior lobe to be one-third of the total volume of the left lung.

In other implementations, the lung segmentation module 104 may segment the lobes by identifying the exterior layer of the lungs and identifying the fissures connecting each of the lobes to one another. To perform this identification, the lung segmentation module 104 may implement artificial intelligence and/or machine learning (supervised or unsupervised), or a neural network.

The system 100 includes a Deformable Image Registration (DIR) module 106 configured to perform DIR operations on the lung-segmented image. The DIR module 106 may compute DIR using the Quadratic Penalty DIR method. The DIR module 106 computes a DIR-computed spatial transformation $\phi: \mathbb{R}^3 \rightarrow \mathbb{R}^3$ that maps the exhale lung geometry onto the inhale lung geometry. The DIR module 106 splits the lung volume into five zones, denoted $\Omega_1, \Omega_2, \ldots \Omega_5$, which are designed to approximate the five lung lobes: $\Omega_1$ is top of right lung, $\Omega_2$ is middle of right lung, $\Omega_3$ is bottom of right lung, $\Omega_4$ is top of left lung, and $\Omega_5$ is bottom of left lung.

The system 100 includes an estimation module 108 configured to perform CTFI-ventilation and perfusion estimation based on the image. The estimation module 108 quantifies ventilation as lung volume change between inhale and exhale and perfusion as the mass change:

$$\text{Vent}\ (\Omega_i) = \left|1 - \frac{vol\ (\phi(\Omega_i))}{vol\ (\Omega_i)}\right|, \tag{1}$$

$$Perf\ (\Omega_i) = \left|1 - \frac{\text{mass}\ (\phi(\Omega_i))}{\text{mass}\ (\Omega_i)}\right|. \tag{2}$$

The estimation module 108 may use an Integrated Jacobian Formulation or any other suitable method to compute the volumes for Eq. 1. The estimation module 108 is configured to approximate material density within the lungs from CT Hounsfield units, and, thus, use this relationship to compute Eq. 2.

The estimation module 108 is configured to model the distinction between functional and non-functional lung zones with threshold parameters. Specifically, each zone $\Omega_i$ has a perfusion threshold, $p_i$, and a ventilation threshold, $v_i$, such that:

$$\begin{aligned} &\text{Low Perfusion: Perf}\ (\Omega_i) < p_i \\ &\text{High Perfusion: Perf}\ (\Omega_i) \geq p_i \end{aligned} \tag{3}$$

and similarly:

$$\begin{aligned} &\text{Low Ventilation: Vent}\ (\Omega_i) < v_i \\ &\text{High Ventilation: Vent}\ (\Omega_i) \geq v_i. \end{aligned} \tag{4}$$

The estimation module 108 is configured to define ventilation/perfusion functional mismatch with respect to an indicator function $B(\Omega_i;p,v)$ that is parameterized by the thresholds:

$$B(\Omega_i; p_i, v_i) = \begin{cases} 0, Perf(\Omega_i) < p_i \text{ and } Vent(\Omega_i) < v_i \text{ (Matched Function)} \\ 0, Perf(\Omega_i) \geq p_i \text{ and } Vent(\Omega_i) \geq v_i \text{ (Matched Function)} \\ 1, Perf(\Omega_i) < p_i \text{ and } Vent(\Omega_i) \geq v_i \text{ (Mismatched Function)} \\ 1, Perf(\Omega_i) \geq p_i \text{ and } Vent(\Omega_i) < v_i \text{ (Mismatched Function)} \end{cases} \tag{5}$$

where $p=(p_1, p_2, p_3, p_4, p_5)$ and $v=(v_1, v_2, v_3, v_4, v_5)$. PE is characterized by the presence of functional mismatch; however, factors including breathing effort variability, 4DCT reconstruction artifacts, and segmentation errors may affect CTFI accuracy, leading to potentially mischaracterized function or an inconclusive result. Additionally, a small amount of ventilation/perfusion mismatch may be common in healthy patients.

Accordingly, the estimation module 108 is configured to cooperate with a PE risk score module 110 to generate and assign a PE risk score to the patient based on the amount of ventilation/perfusion mismatch:

$$PE\ \text{Risk Score} = \begin{cases} \text{Positive, } s(p, v) \geq 3 \\ \text{Inconclusive, } s(p, v) = 2 \\ \text{Negative, } s(p, v) \leq 1 \end{cases}, \tag{6}$$

where the score $$s(p, v) = \sum_{i=1}^{5} B(\Omega_i; p_i, v_i). \tag{7}$$

The PE risk score assigned by the PE risk score module 110 corresponds to a PE diagnosis, i.e., a PE risk score of three or more corresponds to a positive PE diagnosis, a PE risk score equal to two corresponds to an inconclusive PE diagnosis, and a PE risk score of one or less corresponds to a negative PE diagnosis. The PE risk score module 110 may be configured to compare the ventilation estimation and the perfusion estimation to determine the amount of mismatch. The PE risk score module 110 may be configured to generate and display the PE risk score in any suitable manner, e.g., on a display of a computing device, on a printout, etc.

The estimation module 108 and the PE risk score module 110 are configured to determine optimal threshold values:

$$\max_{p,v} \frac{1}{|I_{pos}|} \sum_{j \in I_{pos}} F(s_j(p, v)) + \frac{1}{|I_{neg}|} \sum_{j \in I_{neg}} G(s_j(p, v)), \tag{8}$$

where $$F(x) = \begin{cases} 1, & x \geq 3 \\ 0, & x < 3 \end{cases}, \tag{9}$$

and $$G(x) = \begin{cases} 1, & x \leq 1 \\ 0, & x > 1 \end{cases}. \tag{10}$$

The $j^{th}$ patient's five lung zones are denoted as $\Omega_{ij}$, i=1,2,3,4,5 and Eq. 7 score as $$s(p, v) = \Sigma_{i=1}^{5} B(\Omega_i; p_i, v_i).$$

The index sets of positive and negative patients are denoted as $I_{pos}$ and $I_{neg}$, respectively.

In some implementations, the optimal solution as determined by Eq. 8 may be equal to:

$$\begin{aligned} v^* &= [0.12\ \ 0.15\ \ 0.15\ \ 0.11\ \ 0.12], \\ p^* &= [0.03\ \ 0.10\ \ 0.07\ \ 0.01\ \ 0.13]. \end{aligned} \tag{11}$$

In some implementations, the estimation module 108 and the PE risk score module 110 are configured to determine the PE risk score and/or the optimal threshold values by implementing artificial intelligence and/or machine learning (supervised or unsupervised), or a neural network.

Referring to FIG. 2, a method 200 for executing the system 100 is generally shown. At step 202, the method 200 obtains one or more images of the lungs. For example, the lungs may be provided by a third party, or may be obtained by the system 100 in any suitable manner. At step 204, the method 200 includes defining lung segmentation. For example, the images of the lungs may be segmented into five regions based on the five lobes of the lungs. At step 206, the method 200 includes performing deformable image registration operations. At step 208, the method 200 includes performing CTFI-ventilation and perfusion estimation. At step 210, the method 200 includes generating a PE risk score based on the ventilation and perfusion estimations. For example, the PE risk score may be on a scale between 0 and 5, and the PE risk score may correspond to a PE diagnosis for the patient.

FIG. 3 is a schematic view of an example computing device 300 that may be used to implement the systems and methods described in this document. The computing device 300 is intended to represent various forms of digital computers, such as laptops, desktops, workstations, personal digital assistants, servers, blade servers, mainframes, and other appropriate computers. The components shown here, their connections and relationships, and their functions, are meant to be exemplary only, and are not meant to limit implementations of the inventions described and/or claimed in this document.

The computing device 300 includes a processor 310, memory 320, a storage device 330, a high-speed interface/controller 340 connecting to the memory 320 and high-speed expansion ports 350, and a low speed interface/controller 360 connecting to a low speed bus 370 and a storage device 330. Each of the components 310, 320, 330, 340, 350, and 360, are interconnected using various busses, and may be mounted on a common motherboard or in other manners as appropriate. The processor 310 can process instructions for execution within the computing device 300, including instructions stored in the memory 320 or on the storage device 330 to display graphical information for a graphical user interface (GUI) on an external input/output device, such as display 380 coupled to high speed interface 340. In other implementations, multiple processors and/or multiple buses may be used, as appropriate, along with multiple memories and types of memory. Also, multiple computing devices 300 may be connected, with each device providing portions of the necessary operations (e.g., as a server bank, a group of blade servers, or a multi-processor system).

The memory 320 stores information non-transitorily within the computing device 300. The memory 320 may be a computer-readable medium, a volatile memory unit(s), or non-volatile memory unit(s). The non-transitory memory 320 may be physical devices used to store programs (e.g., sequences of instructions) or data (e.g., program state information) on a temporary or permanent basis for use by the computing device 300. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

The storage device 330 is capable of providing mass storage for the computing device 300. In some implementations, the storage device 330 is a computer-readable medium. In various different implementations, the storage device 330 may be a floppy disk device, a hard disk device, an optical disk device, or a tape device, a flash memory or other similar solid state memory device, or an array of devices, including devices in a storage area network or other configurations. In additional implementations, a computer program product is tangibly embodied in an information carrier. The computer program product contains instructions that, when executed, perform one or more methods, such as those described above. The information carrier is a computer- or machine-readable medium, such as the memory 320, the storage device 330, or memory on processor 310.

The high speed controller 340 manages bandwidth-intensive operations for the computing device 300, while the low speed controller 360 manages lower bandwidth-intensive operations. Such allocation of duties is exemplary only. In some implementations, the high-speed controller 340 is coupled to the memory 320, the display 380 (e.g., through a graphics processor or accelerator), and to the high-speed expansion ports 350, which may accept various expansion cards (not shown). In some implementations, the low-speed controller 360 is coupled to the storage device 330 and a low-speed expansion port 390. The low-speed expansion port 390, which may include various communication ports (e.g., USB, Bluetooth, Ethernet, wireless Ethernet), may be coupled to one or more input/output devices, such as a keyboard, a pointing device, a scanner, or a networking device such as a switch or router, e.g., through a network adapter.

The computing device 300 may be implemented in a number of different forms, as shown in the figure. For example, it may be implemented as a standard server 300*a* or multiple times in a group of such servers 300*a*, as a laptop computer 300*b*, or as part of a rack server system 300*c*.

A software application (i.e., a software resource) may refer to computer software that causes a computing device to perform a task. In some examples, a software application may be referred to as an "application," an "app," or a "program." Example applications include, but are not limited to, system diagnostic applications, system management applications, system maintenance applications, word processing applications, spreadsheet applications, messaging applications, media streaming applications, social networking applications, and gaming applications.

The non-transitory memory may be physical devices used to store programs (e.g., sequences of instructions) or data (e.g., program state information) on a temporary or permanent basis for use by a computing device. The non-transitory memory may be volatile and/or non-volatile addressable semiconductor memory. Examples of non-volatile memory include, but are not limited to, flash memory and read-only memory (ROM)/programmable read-only memory (PROM)/erasable programmable read-only memory (EPROM)/electronically erasable programmable read-only memory (EEPROM) (e.g., typically used for firmware, such as boot programs). Examples of volatile memory include, but are not limited to, random access memory (RAM), dynamic random access memory (DRAM), static random access memory (SRAM), phase change memory (PCM) as well as disks or tapes.

Various implementations of the systems and techniques described herein can be realized in digital electronic and/or optical circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, non-transitory computer readable medium, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

The processes and logic flows described in this specification can be performed by one or more programmable processors, also referred to as data processing hardware, executing one or more computer programs to perform functions by operating on input data and generating output. The processes and logic flows can also be performed by special purpose logic circuitry, e.g., an FPGA (field programmable gate array) or an ASIC (application specific integrated circuit). Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, one or more aspects of the disclosure can be implemented on a computer having a display device, e.g., a CRT (cathode ray tube), LCD (liquid crystal display) monitor, or touch screen for displaying information to the user and optionally a keyboard and a pointing device, e.g., a mouse or a trackball, by which the user can provide input to the computer. Other kinds of devices can be used to provide interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

A number of implementations have been described. Nevertheless, it will be understood that various modifications may be made without departing from the spirit and scope of the disclosure. Accordingly, other implementations are within the scope of the following claims.

What is claimed is:

1. A method for processing images of lungs, the method comprising:

defining, via data processing hardware, lung segmentation of the lungs;

performing, via the data processing hardware, deformable image registration on the segmented lungs;

performing, via the data processing hardware, ventilation estimation operations to determine a ventilation estimation;

performing, via the data processing hardware, perfusion estimation operations to determine a perfusion estimation;

comparing, via the data processing hardware, the ventilation estimation to the perfusion estimation;

determining, via the data processing hardware, a pulmonary embolism risk score based on the comparison of the ventilation estimation to the perfusion estimation; and wherein the pulmonary embolism risk score is determined by:

$$s(p, v) = \sum_{i=1}^{5} B(\Omega_i; p_i, v_i).$$

2. The method of claim 1, wherein the images of the lungs are obtained using non-contrast 4 dimensional computed tomography.

3. The method of claim 1, further comprising receiving, via the data processing hardware, the images of the lungs.

4. A method for processing images of lungs, the method comprising:

defining, via data processing hardware, lung segmentation of the lungs;

performing, via the data processing hardware, deformable image registration on the segmented lungs;

performing, via the data processing hardware, ventilation estimation operations to determine a ventilation estimation;

performing, via the data processing hardware, perfusion estimation operations to determine a perfusion estimation;

comparing, via the data processing hardware, the ventilation estimation to the perfusion estimation;

determining, via the data processing hardware, a pulmonary embolism risk score based on the comparison of the ventilation estimation to the perfusion estimation;

wherein the lungs are segmented into five regions;

wherein the pulmonary embolism risk score is on a scale from 0 to 5 based on the number of lung regions that have ventilation/perfusion mismatch; and wherein ventilation/perfusion mismatch is defined by:

$$B(\Omega_i; p_i, v_i) = \begin{cases} 0, & Perf(\Omega_i) < p_i \text{ and } Vent(\Omega_i) < v_i \text{ (Matched Function)} \\ 0, & Perf(\Omega_i) \geq p_i \text{ and } Vent(\Omega_i) \geq v_i \text{ (Matched Function)} \\ 1, & Perf(\Omega_i) < p_i \text{ and } Vent(\Omega_i) \geq v_i \text{ (Mismatched Function)} \\ 1, & Perf(\Omega_i) \geq p_i \text{ and } Vent(\Omega_i) < v_i \text{ (Mismatched Function)} \end{cases}.$$

5. A method for processing images of lungs, the method comprising:

defining, via data processing hardware, lung segmentation of the lungs;

performing, via the data processing hardware, deformable image registration on the segmented lungs;

performing, via the data processing hardware, ventilation estimation operations to determine a ventilation estimation;

performing, via the data processing hardware, perfusion estimation operations to determine a perfusion estimation;

comparing, via the data processing hardware, the ventilation estimation to the perfusion estimation;

determining, via the data processing hardware, a pulmonary embolism risk score based on the comparison of the ventilation estimation to the perfusion estimation; and wherein optimal threshold values are determined by:

$$\max_{p,v} \frac{1}{|I_{pos}|} \sum_{j \in I_{pos}} F(s_j(p, v)) + \frac{1}{|I_{neg}|} \sum_{j \in I_{neg}} G(s_j(p, v)).$$

6. The method of claim 5, wherein the optimal threshold values obtained from the equation in claim 5 is:

$$v^* = [\,0.12 \;\; 0.15 \;\; 0.15 \;\; 0.11 \;\; 0.12\,],$$

$$p^* = [\,0.03 \;\; 0.10 \;\; 0.07 \;\; 0.01 \;\; 0.13\,].$$

7. The method of claim 1, wherein the pulmonary embolism risk score is determined using one or more of artificial intelligence, machine learning, and a neural network.

8. A system comprising:

data processing hardware; and memory hardware in communication with the data processing hardware, the memory hardware storing instructions that when executed on the data processing hardware cause the data processing hardware to perform operations comprising:

defining lung segmentation of the lungs;

performing deformable image registration on the segmented lungs;

performing ventilation estimation operations to determine a ventilation estimation;

performing perfusion estimation operations to determine a perfusion estimation;

comparing the ventilation estimation to the perfusion estimation; determining a pulmonary embolism risk score based on the comparison of the ventilation estimation to the perfusion estimation; and wherein the pulmonary embolism risk score is determined by:

$$s(p, v) = \sum_{i=1}^{5} B(\Omega_i;\, p_i, v_i).$$

9. The system of claim 8, wherein the images of the lungs are obtained using non-contrast 4 dimensional computed tomography.

10. The system of claim 8, wherein the operations include receiving the images of the lungs.

11. The system of claim 8, wherein the lungs are segmented into five regions.

12. The system of claim 11, wherein the pulmonary embolism risk score is on a scale from 0 to 5 based on the number of lung regions that have ventilation/perfusion mismatch.

13. The system of claim 12, wherein ventilation/perfusion mismatch is defined by:

$$B(\Omega_i;\, p_i, v_i) = \begin{cases} 0, \mathit{Perf}(\Omega_i) < p_i \text{ and } \mathrm{Vent}(\Omega_i) < v_i \text{ (Matched Function)} \\ 0, \mathit{Perf}(\Omega_i) \geq p_i \text{ and } \mathrm{Vent}(\Omega_i) \geq v_i \text{ (Matched Function)} \\ 1, \mathit{Perf}(\Omega_i) < p_i \text{ and } \mathrm{Vent}(\Omega_i) \geq v_i \text{ (Mismatched Function)} \\ 1, \mathit{Perf}(\Omega_i) \geq p_i \text{ and } \mathrm{Vent}(\Omega_i) < v_i \text{ (Mismatched Funciton).} \end{cases}$$

14. The system of claim 8, wherein optimal threshold values are determined by:

$$\max_{p,v} \frac{1}{|I_{pos}|} \sum_{j \in I_{pos}} F(s_j(p, v)) + \frac{1}{|I_{neg}|} \sum_{j \in I_{neg}} G(s_j(p, v)).$$

15. The system of claim 14, wherein the optimal threshold values obtained from the equation in claim 14 is:

$$v^* = [\,0.12 \;\; 0.15 \;\; 0.15 \;\; 0.11 \;\; 0.12\,],$$

$$p^* = [\,0.03 \;\; 0.10 \;\; 0.07 \;\; 0.01 \;\; 0.13\,].$$

16. The system of claim 8, wherein the pulmonary embolism risk score is determined using one or more of artificial intelligence, machine learning, and a neural network.

17. The method of claim 5, wherein the images of the lungs are obtained using non-contrast 4-dimensional computed tomography.

18. The method of claim 5, further comprising receiving, via the data processing hardware, the images of the lungs.

19. The method of claim 5, wherein the lungs are segmented into 5 regions.

20. The method of claim 5, wherein the pulmonary embolism risk score is determined using one or more of artificial intelligence, machine learning, and a neural network.

* * * * *